(12) United States Patent
Raju et al.

(10) Patent No.: US 9,752,998 B1
(45) Date of Patent: Sep. 5, 2017

(54) DETECTING ANOMALIES IN GLASS ARTICLES USING NMR IMAGING

(71) Applicant: Owens-Brockway Glass Container Inc., Perrysburg, OH (US)

(72) Inventors: Ramasamy Raju, Sylvania, OH (US); Pramod K Sharma, Ann Arbor, MI (US)

(73) Assignee: Owens Brockway Glass Container Inc., Perrysburg, OH (US)

( * ) Notice: Subject to any disclaimer, the term of this patent is extended or adjusted under 35 U.S.C. 154(b) by 877 days.

(21) Appl. No.: 14/018,978

(22) Filed: Sep. 5, 2013

(51) Int. Cl.
*G01N 24/08* (2006.01)

(52) U.S. Cl.
CPC .................. *G01N 24/085* (2013.01)

(58) Field of Classification Search
CPC ........ G03G 24/08; G03G 24/085; G01V 3/14; G01R 33/44; G01N 24/085; G01N 15/0656; G01N 27/84
See application file for complete search history.

(56) References Cited

U.S. PATENT DOCUMENTS

| | | | |
|---|---|---|---|
| 2,259,400 A | 10/1941 | Switzer | |
| 2,920,203 A | 1/1960 | Switzer | |
| 3,729,632 A | 4/1973 | Cho et al. | |
| 3,855,526 A * | 12/1974 | Molina | G01N 27/84 324/216 |
| 3,862,047 A * | 1/1975 | Weltman | G01N 27/84 252/62.52 |
| 5,049,819 A | 9/1991 | Dechene et al. | |
| 5,291,422 A | 3/1994 | Esztergar | |
| 6,362,619 B2 | 3/2002 | Prammer et al. | |
| 6,469,507 B1 | 10/2002 | Gerald, II et al. | |
| 6,674,283 B2 | 1/2004 | Gerald, II et al. | |
| 6,759,601 B1 | 7/2004 | Petty et al. | |
| 6,911,822 B2 | 6/2005 | Augustine et al. | |
| 6,946,838 B2 | 9/2005 | Corver et al. | |
| 6,993,972 B2 | 2/2006 | Basir et al. | |
| 7,012,427 B2 | 3/2006 | Augustine et al. | |
| 7,015,693 B2 | 3/2006 | Corver et al. | |
| 7,176,681 B2 * | 2/2007 | Zombo | G01N 24/08 324/301 |
| 7,199,581 B2 | 4/2007 | Corver et al. | |
| 7,339,377 B2 | 3/2008 | Augustine et al. | |
| 7,394,262 B2 | 7/2008 | Manneschi | |
| 7,397,247 B2 | 7/2008 | Kloza et al. | |
| 7,576,538 B2 | 8/2009 | Meersmann et al. | |
| 7,906,975 B2 | 3/2011 | Federici et al. | |
| 8,237,452 B2 | 8/2012 | Federici et al. | |
| 2004/0251904 A1 | 12/2004 | Corver et al. | |
| 2011/0184681 A1 | 7/2011 | Augustine et al. | |

OTHER PUBLICATIONS

A.J. Weekley et al, "Using NMR to Study Full Intact Wine Bottles", Journal of Magnetic Resonance, 161 (2003) 91-98.*
Almanac 2011, Analytical Tables and Product Overview (selected portion for Deuterated and Non-Deuerated agents).*

* cited by examiner

*Primary Examiner* — Clayton E LaBalle
*Assistant Examiner* — Ruifeng Pu

(57) ABSTRACT

A method of inspecting a glass article using nuclear magnetic resonance imaging (NMRI). An NMRI-active filler material may be applied to the interior surface, the exterior surface, or both of the container. The excess material then may be removed leaving the filler within one or more anomalies on the surface of the container. And an NMRI analysis may be performed producing images associated with the anomalies having filler material therein.

7 Claims, 1 Drawing Sheet

DETECTING ANOMALIES IN GLASS ARTICLES USING NMR IMAGING

The present disclosure is directed to a device using an electromagnetic field to detect flaws in a material, and more specifically, detecting surface flaws in the material.

BACKGROUND AND SUMMARY OF THE DISCLOSURE

In the manufacture of containers such as glass bottles and jars, various types of anomalies can occur in the sidewalls, heels, bottoms, shoulders, necks, and finishes of the containers. These anomalies, termed "commercial variations" in the art, can affect commercial acceptability of the containers. Detection of commercial variations in a container can result in rejection of the container, depending upon the type of variation. U.S. Pat. No. 6,104,482 discloses an example of a detection technique for an apparatus that in one embodiment includes a first light source for directing first light energy onto a first portion of the container finish as it is rotated about its axis, and a second light source for directing second light energy onto a second portion of the container finish as it rotates. A first light sensor is disposed with respect to the first light source and the container finish to receive portions of the first light energy reflected from horizontal checks in the container finish. A second light sensor is disposed with respect to the second light source and the container finish to receive portions of the second light energy reflected from vertical checks in the container finish. An information processor is coupled to the first and second sensors for detecting horizontal and vertical checks in the container finish as a function of reflected portions of the first and second light energies. The information processor detects not only presence of reflections from the container finish as a function of position of incidence on the linear array sensor, but also angular position of the reflections as a function of container rotation.

A general object of the present disclosure, in accordance with one aspect of the disclosure, is to detect anomalies in a glass article.

The present disclosure embodies a number of aspects that can be implemented separately from or in combination with each other.

In accordance with one aspect of the present disclosure, a method of inspecting a glass article includes applying a contrast agent to a surface of the glass article, removing excess material leaving the contrast agent in surface anomalies of the glass article, and subjecting the article to nuclear magnetic resonance (NMR) analysis to form images of the surface anomalies retaining the contrast agent.

In accordance with another aspect of the present disclosure, a method of performing quality control for containers, which includes the steps of scanning a plurality of containers having a NMRI-active filler material applied thereto, and providing at least one image based on the scanning step of one of the plurality of containers, wherein at least one image reveals a micro-sized anomaly.

BRIEF DESCRIPTION OF THE DRAWINGS

The disclosure, together with additional objects, features, advantages and aspects thereof, will be best understood from the following description, the appended claims and the accompanying drawings, in which:

DETAILED DESCRIPTION OF PREFERRED EMBODIMENTS

Figure 1:
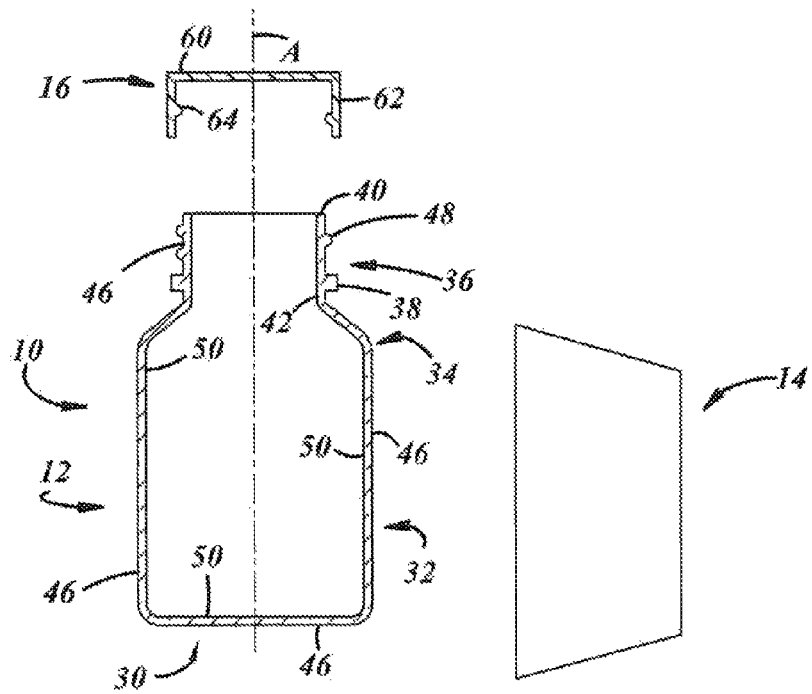
FIG. 1 is a schematic diagram of an inspection system in accordance with an illustrative embodiment of the present disclosure and illustrating a sectional view of a container and closure and an NMRI device.

The following detailed description discloses a method of detecting anomalies in an article or target object using nuclear magnetic resonance imaging (NMRI). In one embodiment shown in FIG. 1, the article or object is a container 12. The illustrated embodiment shows a package 10 that includes the container 12 and a closure 16 in proximity of a NMRI system 14, as will be discussed in further detail herein below. The container 12 may be composed of metal, plastic, glass, or any other suitable material and, more particularly, may be produced in accordance with illustrative embodiments of a glass manufacturing process disclosed herein below.

The container 12 may be of any suitable shape, and may include a jug, jar, bottle, other food or beverage container, or any other suitable container. The container 12 may include a base 30 at one axial end upon which the container may be supported, a body 32 extending axially from the base 30, a shoulder 34 extending radially and axially from the body 32, and a neck 36 extending axially from the shoulder 34. As used herein, the term axial includes oriented generally along a longitudinal axis of the closure, container, or package and may include but is not limited to a direction that is strictly parallel to a container longitudinal central axis A.

The body 32 and neck 36 may be generally cylindrical, as illustrated, or they may be tapered or of any other suitable shape. The neck 36 may include a capping flange or bead 38, a junction 42 between the shoulder 34 and the neck 36, and an axial outward end surface 40. The neck 36 may include one or more closure retention elements 48 projecting from an external surface 46, or the like, for cooperation with corresponding portions of the closure 16. The elements 48 may include threads or thread segments, as illustrated, or bayonet features, snap-fit features, or any other suitable closure retention features. As used herein, the term thread segment includes whole, partial, multiple, and/or an interrupted thread, thread segment, and/or lug. The exterior surface 46 may include all outwardly facing surfaces on the base 30, body 32, shoulder 34, and neck 36 (including elements 48 and the end surface 40). An interior surface 50 of the container 12 may include all inwardly facing surfaces; e.g., the inwardly facing surfaces of the base 30, the body 32, the shoulder 34, and the neck 36.

The container 12 may be of one-piece integrally formed construction, preferably glass, metal, or plastic construction. (The term "integrally formed construction" does not exclude one-piece integrally molded layered glass constructions of the type disclosed for example in U.S. Pat. No. 4,740,401, or one-piece glass bottles to which other structure is added after the bottle-forming operation.) In one embodiment, the container 12 may be fabricated in press-and-blow or blow-and-blow glass container manufacturing operations.

The closure 16 may be any suitable device for retaining the contents or product of the container 12. As shown in FIG. 1, the closure 16 may include a cap, cork, plug, or any other suitable type of closure, and may be composed of plastic, metal, glass, ceramic, or any other suitable material. In any case, the closure 16 may include a base wall 60 and an annular outer skirt 62 extending from the base wall 60 and having one or more internal container retention elements 64 projecting from an internal surface thereof for cooperation with corresponding portions of the container 12. The elements 64 may include threads or thread segments, as illustrated, or bayonet features, snap-fit features, or any other suitable container retention features. Furthermore, some embodiments of the package may not include the closure 16.

Also shown in FIG. 1 is the nuclear magnetic resonance imaging (NMRI) system 14 that includes a powerful magnet, a scanning device for scanning and/or imaging a target object, and a memory device. The system 14 further includes any additional equipment and/or instrumentation for nuclear magnetic resonance (NMR) analysis including emitting and/or controlling a magnetic field in a target region and/or determining one or more measurements based on the emitting, scanning, and/or imaging. For example, the magnetic field of the powerful magnet may be used to align the magnetization of the atomic nuclei in a filler material and radio frequency fields may be used to systematically alter the alignment of this magnetization, as will be explained in greater detail below. This causes the nuclei to produce a rotating magnetic field detectable by the scanning device, and this data or information is recorded in the memory device to construct an image of the scanned area of the target object. Magnetic field gradients may cause nuclei at different locations to rotate at different speeds. By utilizing these gradients in different directions, 2-dimensional (2D) images or 3-dimensional (3D) images may be obtained in any arbitrary orientation (e.g., of the target object). Persons of ordinary skill in the art will appreciate various implementations and components of the system 14 and the various processes and techniques for using the system (e.g., scanning, imaging, etc.).

In FIG. 1, the container 12 is illustrated as the target object. While the NMRI system 14 is oriented with respect to the body 32 of the container, it also should be appreciated that the system 14 may be used to measure other regions of the container 12 (i.e., the base 30, the shoulder 34, and the neck 36). In addition, the system 14 is shown located outside of the container 12; however, the system 14 and/or various components of the system 14 may be located inside the container 12 in some implementations.

As previously discussed, the container 12 may be manufactured glass. In production, and generally speaking, typical glass container manufacturing includes a "hot end" and a "cold end." The hot end may include one or more glass melting furnaces to produce a glass melt, one or more forming machines to form the glass melt into glass containers, and one or more applicators to apply a hot-end coating to the glass containers. The "hot end" also may include an annealing lehr, or at least a beginning portion of the annealing lehr, for annealing the glass containers therein. Through the lehr, the temperature may be brought down gradually to a downstream portion, cool end, or exit of the lehr. The "cold end" may include an end portion of the annealing lehr, applicators to apply one or more cold-end coatings to the glass containers downstream of the annealing lehr, inspection equipment to inspect the containers, and packaging machines to package the containers.

In conjunction with the above description, the container 12 may be produced by the following glass container manufacturing process, which may or may not include all of the disclosed steps or be sequentially processed or processed in the particular sequence discussed, and the presently disclosed manufacturing process and marking methods encompass any sequencing, overlap, or parallel processing of such steps.

First, a batch of glass-forming materials may be melted. For example, a melting furnace may include a tank with melters to melt soda-lime-silica to produce molten glass. Thereafter, the molten glass may flow from the tank, through a throat, and to a refiner at the downstream end of the furnace where the molten glass may be conditioned. From the furnace, the molten glass may be directed toward a downstream forehearth that may include a cooling zone, a conditioning zone, and a downstream end in communication with a gob feeder. The feeder may measure out gobs of glass and deliver them to a glass container forming operation.

Next, the glass gobs may be formed into containers, for example, by forming machines, which may include press-and-blow or blow-and-blow individual section machines, or any other suitable forming equipment. Blank molds may receive the glass gobs from the feeder and form parisons or blanks, which may be at a temperature, for example, on the order of 900-1100 degrees Celsius. Blow molds may receive the blanks from the blank molds and form the blanks into glass containers, which may be at a temperature, for example, on the order of 700-900 degrees Celsius. Material handling equipment may remove the glass containers from the forming machines and place the containers on conveyors or the like.

Also, the formed glass containers may be annealed, for example, by an annealing lehr. At an entry, hot end, or upstream portion of the annealing lehr, the temperature therein may be, for instance, on the order of 500-700 degrees Celsius. During this period of time, one or more coatings may be applied to the container 12 (e.g., at or near the neck 36). Through the lehr, the temperature may be brought down gradually to a downstream portion, cool end, or exit of the lehr, to a temperature therein, for example, on the order of 65-130 degrees Celsius.

Figure 2:
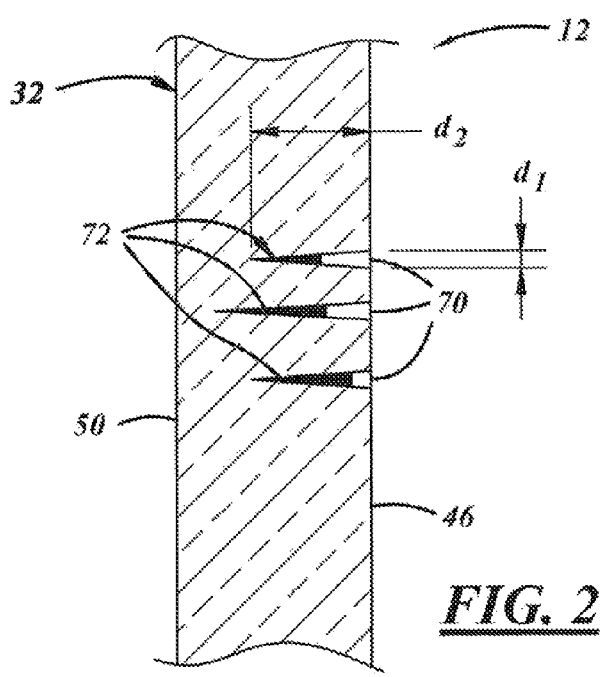
FIG. 2 is an enlarged fragmentary view of the container shown in FIG. 1.

During or following the glass container manufacturing process, some containers may contain one or more anomalies shown in FIG. 2 which illustrates an enlarged, fragmentary view of the body 32 of the container 12 shown in FIG. 1. The anomalies may be located at the interior and/or exterior surface(s) 50, 46 of the container 12. FIG. 2 illustrates several anomalies 70 located on the exterior surface 46 of the container extending inwardly towards the interior surface 50. Of course, one or more anomalies 70 could extend outwardly from the interior surface 50 towards the exterior surface 46. In addition, the anomalies 70 could extend from an inclusion such as a stone or other foreign particle (not shown) located between the interior and exterior surfaces 50, 46; e.g., indicating the presence of the inclusion. As used herein, the term anomalies should be construed broadly to include any flaw, crack, fissure, separation, cavity, crevice, void, or gap on the exterior surface 46 or the interior surface 50. The size of the anomalies may vary as well; e.g., in at least one implementation, an opening $d_1$ of an anomaly may be sized between 0.5 microns and 100 microns, and a depth $d_2$ of an anomaly may be between 1 and 300 microns. In FIG. 2, at least a portion of the anomalies 70 are shown having a contrast agent or filler material 72 therein. The contrast agent may be any substance used in conjunction with the NMRI system 14 to identify anomalies in the container 12—e.g., to contrast the anomaly against the general contour or shape of the exterior or interior surface 46, 50 of the container 12. In one illustrative implementation, the contrast agent 72 is an NMRI-active filler material responsive to the magnetic field emitted by the NMRI system 14. The filler material 72 may enable the system 14 to determine, detect, scan, and/or image the anomalies 70, as will be explained in greater detail below. A few examples of contrast agents 72 are shown in Table I, more specifically, non-isotropic fillers and deuterated isotropic fillers. It should be appreciated that the illustrated materials are merely examples and that other materials or substances also may be used (e.g., materials having NMRI active nuclei include 1 H, 13 C, 19 F, 31 P, 2 Fl, 6 Li, 14 N, 23 Na, 19 Si, 35 Cl, and 37 Cl).

TABLE I

| Nature of Contrast Agent | Material |
| --- | --- |
| Non-Isotopic Fillers | Dimethyl Sulfoxide (DMSO) |
|  | Acetic Add |
|  | Aceton |
|  | Acetonitrile |
|  | Benzene |
|  | Chloroform |
|  | Chlorobenzene |
|  | Cyclohexane |
|  | N,N Dimethylformamide (DMF) |
|  | Methanol |
| Isotopic Fillers (Deuterated) | Dimethyl Sulfoxide-d6 |
|  | Acetic Acid-d4 |
|  | Aceton-d6 |
|  | Acetonitrile-d3 |
|  | Benzene-d6 |
|  | Chloroform-d |
|  | Chlorobenzene-d5 |
|  | Cyclohexane-d12 |
|  | N,N Dimethylformamide-d7 |
|  | Methanol-d4 |

Now turning to a method for inspecting the container 12, according to one illustrative embodiment of the present disclosure. A first step may include receiving or providing the container 12; e.g., in one example, the container 12 may be a manufactured glass container or article provided by the described process above. The containers 12 may be provided singly or in greater quantities (e.g., on a production or assembly line).

After receipt of the container(s) 12, the contrast agent 72 may be applied to at least a portion of one surface of the glass container 12. Application to the exterior and/or interior surfaces 46, 50 may include spraying the container(s) 12 with the agent 72 or dipping them in the agent 72 or allowing the agent 72 to flow over the container(s) 12 (i.e., over-flowing). The contrast agent 72 may be selected from Table I or may include any other suitable material or substance. During the application, it will be desirable to locate the contrast agent 72 within the anomalies 70. The anomalies 70 may be either partially or entirely filled or penetrated with the contrast agent 72, and persons of ordinary skill in the art will appreciate other various techniques and methods used to apply the contrast agent 72.

After application, any excess contrast agent may be removed from the container 12. The excess material may include contrast agent upon the internal and/or external surface 50, 46 of the container 12 but not located in the anomalies 70. Removal of the excess material may include removing all of the excess material from the interior and/or exterior surfaces 46, 50 and leaving at least 1-20% of the contrast agent (e.g., the residual or remaining contrast agent 72) within the anomalies 70. In at least one implementation, the excess material may be removed by wiping the glass container 12 or allowing the excess material to evaporate (e.g., evaporation using air-drying, heating, blowing, etc.).

Next, the container 12 may be subjected to NMR analysis using the NMRI system 14. For example, the residual contrast agent 72 within the anomalies 70 may be detectable and/or imageable. More specifically, as shown in FIG. 2, where the residual contrast agent 72 remains located in the anomalies 70, the anomalies 70 may be detected and imaged. In one implementation, the NMRI system 14 may produce a magnetic field that aligns the atomic nuclei of the contrast agent 72.

Following NMR analysis, the containers 12 may or may not be washed and/or cleaned. The washing may remove any remaining excess contrast material 72 on the internal and/or external surfaces 50, 46 (where residual contrast material was not entirely removed prior to NMR analysis and imaging). In addition, any residual contrast material 72 located within or at the anomalies 70 may also be removed.

The NMRI system 14 may be used for manufacturing quality control and may enable detection and imaging of potential anomalies 70 without damaging the target object—e.g., the container 12. The NMRI system 14 is capable of detecting micro-sized anomalies 70 that may not be perceptible to the human-eye, e.g., micron sized anomalies introduced during the formation and handling process of high-volume glass container manufacturing. The system 14 may be capable of providing data or other suitable information pertaining to the nature and details of any detected or imaged anomalies—including surface and/or bulk anomalies. In addition to high-speed scanning capability, the NMRI system 14 is suitable for scanning the varying surface areas associated with glass containers; e.g., containers having common and/or eccentric shapes and contours. The system 14 may provide 2-dimensional (2D) images, 3-dimensional (3D) images, or both.

In one implementation, the NMRI system 14 may be utilized at the glass manufacturing facility. This may enable on-site detection of and root-cause determination of the anomalies 70, thereby enabling continuous process improvement to glass manufacturing. In at least one implementation, the NMRI system 14 and methods described herein may be used during the glass container manufacturing process; e.g., the application of the contrast agent, removal of the excess material, and NMRI analysis may be conducted after the container 12 leaves the hot end and before it enters the cold end. In other implementations, the NMRI system 14 may be used at a bottling or packing plant. However, the NMRI system 14 is merely illustrative and other suitable nondestructive detection/imaging techniques (NDTs) also may be used; e.g., optical, chemical, and other radiation techniques.

Thus there has been disclosed methods of analyzing one or more glass articles, that fully satisfy all of the objects and aims previously set forth. The disclosure has been presented in conjunction with several illustrative embodiments, and additional modifications and variations have been discussed. Other modifications and variations readily will suggest themselves to persons of ordinary skill in the art in view of the foregoing discussion. For example, the presently disclosed method has been discussed in terms of a container composed of glass and glass container manufacturing process, but the disclosure likewise may apply to other glass articles, as well as plastic and plastic container manufacturing. The disclosure is intended to embrace all such modifications and variations as fall within the spirit and broad scope of the appended claims.

The invention claimed is:

1. A method of inspecting a glass container, which includes the steps of:
    (a) applying a contrast agent to a surface of the glass container by at least one of spraying the glass container with the contrast agent or dipping the glass container in the contrast agent, and then (b) removing excess material applied in said step (a) leaving the contrast agent in surface anomalies of the glass container by at least one of wiping, air-drying, heating, or blowing the glass container, and then (c) subjecting the glass container to nuclear magnetic resonance (NMR) analysis to form images of the surface anomalies retaining the contrast agent, and then (d) washing the glass container to remove the contrast agent.

2. The method set forth in claim 1 wherein said surface is an exterior surface or an interior surface of the container.

3. The method set forth in claim 1 wherein said contrast agent is an NMRI-active filler material.

4. The method set forth in claim 3 wherein said filler material is a deuterated isotopic filler material including at least one of the following materials: Dimethyl Sulfoxide-d6; Acetic Acid-d4; Aceton-d6; Acetonitrile-d3; Benzene-d6; Chloroform-d; Chlorobenzene-d5; Cyclohexane-d12; N,N Dimethylformamide-d7; or Methanol-d4.

5. The method set forth in claim 3 wherein said filler material is an non-isotopic filler material including at least one of the following materials: Dimethyl Sulfoxide (DMSO); Acetic Acid; Aceton; Acetonitrile; Benzene; Chloroform; Chlorobenzene; Cyclohexane; N,N Dimethylformamide (DMF); or Methanol.

6. The method set forth in claim 3 wherein said filler material is at least one of the materials listed in Table I.

7. The method set forth in claim 1, further comprising the step of forming the glass container before step (a), and wherein step (c) is carried out before the glass container enters a cold end of a glass container manufacturing process.

\* \* \* \* \*